United States Patent
Hong et al.

(10) Patent No.: US 11,077,066 B2
(45) Date of Patent: Aug. 3, 2021

(54) PH-SENSITIVE STARCH-BASED MICROCAPSULE AND ITS PREPARATION METHOD

(71) Applicant: Jiangnan University, Wuxi (CN)

(72) Inventors: Yan Hong, Wuxi (CN); Min Jiang, Wuxi (CN); Zhengbiao Gu, Wuxi (CN); Li Cheng, Wuxi (CN); Zhaofeng Li, Wuxi (CN); Caiming Li, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 16/720,223

(22) Filed: Dec. 19, 2019

(65) Prior Publication Data

US 2020/0121609 A1    Apr. 23, 2020

Related U.S. Application Data

(63) Continuation of application No. PCT/CN2019/086180, filed on May 9, 2019.

(51) Int. Cl.
| | | |
|---|---|---|
| *A61K 9/50* | (2006.01) | |
| *A61K 31/355* | (2006.01) | |
| *A23P 10/30* | (2016.01) | |
| *A23L 33/10* | (2016.01) | |
| *A23L 29/219* | (2016.01) | |
| *A23L 33/12* | (2016.01) | |
| *A23L 33/15* | (2016.01) | |

(52) U.S. Cl.
CPC .......... *A61K 9/5036* (2013.01); *A23L 29/219* (2016.08); *A23L 33/10* (2016.08); *A23L 33/12* (2016.08); *A23L 33/15* (2016.08); *A23P 10/30* (2016.08); *A61K 9/5089* (2013.01); *A61K 31/355* (2013.01); *A23V 2002/00* (2013.01)

(58) Field of Classification Search
None
See application file for complete search history.

(56) References Cited

FOREIGN PATENT DOCUMENTS

| | | |
|---|---|---|
| CN | 103948565 A | 7/2014 |
| CN | 104721167 A | 6/2015 |
| CN | 108148444 A | 6/2018 |
| CN | 108651996 A | 10/2018 |
| CN | 109452621 A | 3/2019 |

OTHER PUBLICATIONS

English translation for CN103948565A (Year: 2014).*
English translation for CN104721167A (Year: 2015).*
Kwon et al "Physicochemical Properties and Functionality of Highly Carboxymethylated Starch", Starch, vol. 49 (12), p. 499-505. (Year: 1997).*

* cited by examiner

*Primary Examiner* — Sin J Lee
(74) *Attorney, Agent, or Firm* — IPro, PLLC

(57) ABSTRACT

The present disclosure discloses a pH-sensitive starch-based microcapsule encapsulating a fat-soluble substance and a preparation method thereof, and belongs to the field of preparation of starch-based hydrogel microcapsules. The method of the present disclosure comprises performing acid hydrolysis on starch to obtain acid-hydrolyzed carboxymethyl starch, mixing the acid-hydrolyzed carboxymethyl starch with xanthan gum to obtain a compounded solution of starch and colloid, adding an emulsifier and the fat-soluble substance, emulsifying to obtain an emulsion, and drying to obtain the microcapsule. The microcapsule prepared by the preparation method of the present disclosure is capable of resisting hydrolysis by gastric acid and enzymes in gastric juice and improving the bioavailability of core materials, namely the fat-soluble substances; has a release rate of only 20 to 40% in simulated gastric juice, while having a cumulative release rate of 80 to 95% in the upper digestive tract (simulated gastric juice and simulated intestinal juice) of a human body; solves the problems that the fat-soluble substance is poor in water solubility, prone to oxidation, low in oral availability and the like; can be added to products such as beverages and the like as a nutrient supplement or a food additive, and has wide application prospects.

16 Claims, 3 Drawing Sheets

PH-SENSITIVE STARCH-BASED MICROCAPSULE AND ITS PREPARATION METHOD

TECHNICAL FIELD

The present disclosure relates to a pH-sensitive starch-based microcapsule and its preparation method, and belongs to the field of preparation of starch-based microcapsules.

BACKGROUND

At present, there are more and more researches on functional substances in the food field. There are 11 types of functional substances have been identified in food, which are mainly divided into two categories: fat-soluble functional substances and water-soluble functional substances. The fat-soluble functional substances are predominant, and the special efficacy thereof is mainly concentrated in anti-oxidation, anti-virus, blood fat and blood sugar reduction, immunity improvement, and growth and development promotion, etc. At the same time, in the actual application process, the fat-soluble functional substances also have many defects such as poor dispersion, sensitivity to light, heat and oxygen, unpleasant odor and susceptibility to damages caused by the upper digestive tract of the human body. Therefore, finding a method which not only retains the efficacy of the fat-soluble functional substances but also improves the bioavailability thereof is the key to solving the problems.

Stabilization techniques for encapsulating and protecting the fat-soluble functional substances mainly include an adsorption method, a microcapsule encapsulating method, a crosslinking method, and a carrier-binding method. The microcapsule encapsulating method is currently the most widely used stabilization method in the food field, and has the characteristics of being capable of changing the state, mass, volume and properties of materials, protecting sensitive components, enhancing stability, controlling the release of core materials, reducing or masking unpleasant odor, reducing volatility, and separating components. Materials that have been reported to be capable of being used as microcapsule carriers mainly include: synthetic polymers, composite materials, vegetable gums, proteins, dextrins, and starch and derivatives thereof. There have been many reports on the use of the above-mentioned carrier materials to encapsulate functional substances and to achieve slow and controlled release by means of microencapsulation. However, the bioavailability of the functional substances is still incomplete because most of the fat-soluble substances are absorbed in the small intestine, if the resistance of a wall material to acid and enzymatic hydrolysis is not strong, a large part of active substances will be destroyed by strong acid or enzymes in the stomach before reaching the small intestine (especially duodenum and ileum of the upper part of the small intestine); in addition, if the resistance of the wall material to acid and enzymatic hydrolysis is too strong, the active substances cannot be fully utilized in the colon, and will be excreted along with human metabolism after 24 hours. These all will lead to problems such as low bioavailability of the functional substances, thus restricting the application of microcapsules of fat-soluble functional substances. Therefore, in view of the difference in pH values of human gastric juice and intestinal juice, in order to achieve less release of functional substances in gastric juice but more release in intestinal tract, a microcapsule carrier is required to have certain sensitivity to pH. At present, this is also a hotspot and difficulty of research and development for workers in this field.

Hydrocolloids have general properties of long-chain polymers, but contain more functional groups than general polymers, and exhibit unique properties under specific conditions. The main physical and chemical properties include: the hydrocolloids are easily soluble in hot and cold water, have good thickening property, maintain high pseudoplasticity within a relatively wide range of concentration and shear rate, and are relatively stable to heat, etc., and the most important aspect is that the hydrocolloids have strong resistance to acid and enzymatic hydrolysis. Therefore, by compounding the hydrocolloids with starch, a carrier is enabled to have certain resistance to acid and enzymatic hydrolysis, thereby protecting the fat-soluble substances and transporting the fat-soluble substances to the absorption site of the human body—the small intestine.

As a renewable resource, starch is a wide in sources and low in price. There are various deep-processing products using starch as a raw material. If starch is used as the wall material of a microcapsule, the disadvantages that other materials are expensive and in short supply can be made up, and it is conducive to the development of the starch industry. Current reports on the realization of sustained release in gastrointestinal tract include patent CN106509899A, which discloses that debranched starch was used as a main material to be combined with xanthan gum to encapsulate tea polyphenols so as to realize the sustained release of tea polyphenols in the gastrointestinal tract. However, the sustained release effect of the method is not very satisfactory, which is shown in the following aspects: (1) the release amount of tea polyphenols in simulated gastric juice is too large; (2) an increase of the proportion of xanthan gum can reduce the release amount of tea polyphenols in the simulated gastric juice, but making the release of tea polyphenols be incomplete in simulated intestinal juice; and (3) functional substances in food are mostly fat-soluble substances, so that the patent does not have universality. Therefore, there is an urgent need to construct a natural non-toxic pH-responsive starch-based microcapsule carrier model to achieve the intestine-targeted release of fat-soluble substances.

SUMMARY

In order to solve the above problems, the present disclosure constructs a pH-sensitive carrier, which encapsulates a fat-soluble substance by regulating the three-dimensional network structure of the carrier to achieve the purpose of pH-sensitive release from simulated gastric juice to simulated intestinal juice, and increase the release amount of the functional substance in small intestine, thereby increasing the oral availability and bioavailability.

Natural starch molecules contain a large amount of active hydroxyl groups, and various chemical reactions can be carried out to obtain starch derivatives with new functions. Therefore, it is a key technology of the present disclosure to construct a pH-sensitive starch-based carrier by performing carboxymethylation modification on the natural starch and introducing an anionic ionizable group, namely a carboxyl group.

The present disclosure uses acid hydrolyzed-carboxymethyl starch and a hydrophilic colloid as main raw materials to prepare a microcapsule, and uses the —$CH_2COOH$ group carried by the carboxymethyl starch to generate protonation and deprotonation reactions according to a difference between pH values of the digestive tract in a human body, which allows that the network structure of the microcapsule carrier is relatively dense in gastric juice, while relatively loose in small intestine juice, thereby achieving the effect of pH-sensitive release of the fat-soluble substances.

A first objective of the present disclosure is to provide a preparation method of a pH-sensitive starch-based microcapsule encapsulating a fat-soluble substance, the method includes: performing acid hydrolysis and etherification on starch to obtain acid-hydrolyzed carboxymethyl starch, mixing the acid-hydrolyzed carboxymethyl starch with a hydrophilic colloid to obtain a compounded solution of starch and colloid, adding an emulsifier and a fat-soluble functional substance, emulsifying to obtain an emulsion, and drying to obtain the pH-sensitive starch-based microcapsule.

In one embodiment of the present disclosure, the starch includes one or more of corn starch, potato starch, tapioca starch, waxy corn starch, pea starch, wheat starch, rice starch, and the like.

In one embodiment of the present disclosure, the acid-hydrolyzed carboxymethyl starch has a degree of substitution of 0.2 to 0.6.

In one embodiment of the present disclosure, the hydrophilic colloid includes one or more of guar gum, xanthan gum, arabic gum, carrageenan, gellan gum, and the like.

In one embodiment of the present disclosure, the mass fraction ratio of the acid-hydrolyzed carboxymethyl starch to xanthan gum is (5-40):1.

In one embodiment of the present disclosure, the fat-soluble substance includes one or more of vitamin E, lycopene, β-carotene, conjugated linoleic acid, docosahexaenoic acid (DHA), eicosapentaenoic acid (EPA), and the like.

In one embodiment of the present disclosure, the ratio of the amount of the fat-soluble substance to the sum of masses of the acid-hydrolyzed carboxymethyl starch and the hydrophilic colloid in the compounded solution (core-to-wall ratio) is 1:4 to 1:10.

In one embodiment of the present disclosure, the emulsion has a solid content of 5% to 25%.

In one embodiment of the present disclosure, the starch is added to a hydrochloric acid solution with a certain concentration, and reacted at a controlled temperature in a thermostatic water bath to obtain a finished product of acid-hydrolyzed starch. Different degrees of acid hydrolysis affect the release of the fat-soluble functional substance and the synergistic effect of compounding with the xanthan gum. Subsequently, 80% to 95% ethanol and acid-hydrolyzed starch are added to prepare acid-hydrolyzed carboxymethyl starch with different degrees of substitution in an organic phase system under certain pH value and temperature conditions by adjusting sodium hydroxide and an etherifying agent, namely monochloroacetic acid.

In one embodiment of the present disclosure, the preparation method of the pH-sensitive starch-based microcapsule includes:

(1) Dissolving acid-hydrolyzed carboxymethyl starch with different degrees of substitution in water and sufficiently hydrating to form a homogeneous solution; then uniformly dispersing xanthan gums of different ratios in the acid-hydrolyzed carboxymethyl starch solution to prepare a compounded solution of starch and colloid.

(2) Adding an emulsifier, namely Tween-80 into the compounded solution prepared in the step (1), stirring on a magnetic stirrer for 5 to 10 min; then adding a certain amount of fat-soluble functional substance to the solution, performing high-speed shearing using a high-speed shearing machine at 10000 to 20000 r/min for 2 to 5 min to obtain a crude emulsion, then performing cyclical homogenization 3 to 5 times by a high-pressure homogenizer at 200 to 400 bar to obtain an emulsion.

(3) Performing spray-drying on the emulsion obtained in the step (2), wherein the inlet air temperature is 145-165° C., the outlet air temperature is 75-95° C., and the feed rate is 400-600 mL/h; stirring while performing spray-drying in dark to obtain a microcapsule of the fat-soluble functional substance.

A second objective of the present disclosure is to provide a pH-sensitive microcapsule encapsulating a fat-soluble substance; the pH-sensitive microcapsule is prepared by the above method.

A third objective of the present disclosure is to provide a nutrient supplement including the above pH-sensitive microcapsule.

In one embodiment of the present disclosure, the nutrient supplement further includes auxiliary materials.

In one embodiment of the present disclosure, the auxiliary materials include a seasoning agent, a solubilizer and a colorant.

A fourth objective of the present disclosure is to provide a food additive including the above pH-sensitive microcapsule.

In one embodiment of the present disclosure, the food additive can be applied to beverages, dough, sauces, meat products, reconstituted food products, etc.

The beneficial technical effects of the present disclosure include:

1. The acid-hydrolyzed carboxymethyl starch used in the present disclosure is double-modified anionic etherified starch which not only has low viscosity after being dissolved in water, but also has an ionizable —COOH (carboxyl) group, can realize the contraction or extension of the starch molecular segments according to the change of the environmental pH value, thereby altering the permeability of the microcapsule carrier to a dissolution medium. By using the feature, burst release of the fat-soluble functional substances in the upper part of the small intestine can be realized.

2. In the present disclosure, a carboxymethyl group is introduced into the starch molecule, which makes it easily combined with water, and the particles swell and gelatinize with water, so the average digestion rate of total carbohydrates of the carboxymethyl starch particles is greater than that of original starch particles. Therefore, the anti-enzymatic starch content of the carboxymethyl starch is lower than that of the original starch. Hydrocolloid, as a macromolecular substance that can be dissolved in water, can form a certain synergistic effect with starch after being combined in a proper ratio, and obviously improves the acid resistance and enzymatic resistance of starch, thereby resisting to the hydrolysis of gastric acid and enzymes in gastric juice and improving the bioavailability of the core material, namely the fat-soluble functional substance. The release rate in simulated gastric juice is only 20 to 40%, and the cumulative release rate in the upper digestive tract (simulated gastric juice and simulated intestinal juice) in the human body is up to 80 to 95%.

3. The microcapsule technology used in the present disclosure can effectively reduce the damage of external environmental factors (such as light, oxygen, water) to active substances, enhance the water solubility of the fat-soluble substance, reduce the damage of functional substance in stomach, increase the release rate of the functional substance at the upper end of the small intestine and thereby improving the bioavailability thereof. The method of the present disclosure adopts a novel starch-based microcapsule carrier— acid-hydrolyzed carboxymethyl starch and xanthan gum to prepare a microcapsule by spray-drying, thereby solving the problem that the fat-soluble substance is poor in water solubility, prone to oxidation, low in oral availability and the like. Furthermore, since the acid-hydrolyzed carboxymethyl starch per se has a certain viscosity after being dissolved in water, the prepared microcapsule can be added as a nutrient supplement to beverages and the like.

DETAILED DESCRIPTION

Figure 1:
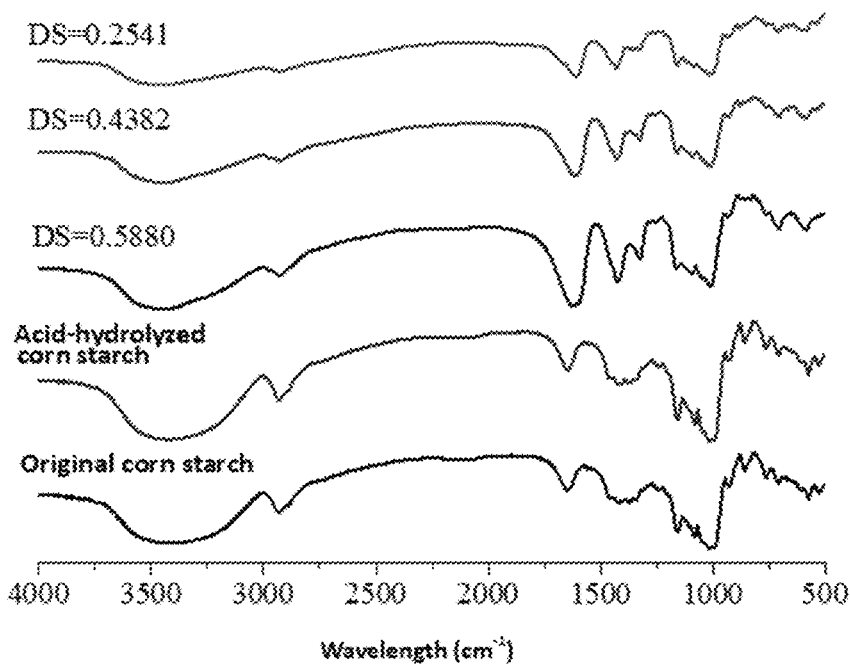
FIG. 1 is an infrared spectrum of an acid-hydrolyzed carboxymethyl starch assembled carrier material.

Exemplary embodiments are described hereinbelow in more detail so that the present disclosure will be thorough and complete, and the exemplary embodiments fully convey the scope of the present disclosure to those skilled in the art.

Preparation of Acid-Hydrolyzed Carboxymethyl Starch:

(1) Acid hydrolysis: a certain amount of starch was accurately weighed and added to 1.0 mol/L of HCl solution to prepare a starch milk with a mass concentration of 40% (on a dry basis), the starch milk was placed in a thermostatic water bath at 45° C. for acid hydrolysis for 2 hours, then the pH of the reaction system was adjusted to about 6.5 with 0.75 mol/L of NaOH solution to end the reaction. The mixture was placed in a centrifuge to be centrifuged at 4500 r/min for 10 min, and centrifugally washed for 3 times. The washed sample was dried in an air dry oven at 45° C. for 18 h, pulverized and passed through a 100-mesh sieve to obtain a finished product of acid-hydrolyzed starch.

(2) Etherification: 80% to 95% ethanol was added to a four-necked flask; 80 to 120 g of acid-hydrolyzed starch on dry basis was added while stirring; dissolved NaOH was slowly added; the thermostatic water bath was turned on for alkalization at 40-50° C. for 30 to 120 min; then 64.8 to 97.2 g of solid chloroacetic acid was added for etherification; the reaction was controlled to etherify at 40 to 60° C. for 2 to 5 h; the mixture was neutralized to neutral with glacial acetic acid, washed multiple times with 95% ethanol, subjected to suction filtration, dried at 45° C. for 2 to 4 h, and pulverized to obtain the acid-hydrolyzed carboxymethyl starch.

Degree of substitution: degree of substitution refers to the number of hydroxyl groups substituted by carboxymethyl groups in each anhydroglucose unit in the starch molecule.

Example 1

A preparation method of a pH-sensitive microcapsule encapsulating vitamin E, which uses acid-hydrolyzed carboxymethyl starch and xanthan gum as wall materials, and includes the following specific steps:

(1) 4.0 g of xanthan gum was uniformly dispersed in 575.05 g of water, and stirred for 90 min to enable the colloid to be uniformly dispersed, so as to obtain a colloidal solution;

(2) 86.75 g of acid-hydrolyzed carboxymethyl starch with a degree of substitution of 0.5880 was weighed, added to the colloidal solution prepared in the step (1) and stirred for 90 min to enable the sample to be uniformly mixed, so as to obtain a compounded solution of acid-hydrolyzed carboxymethyl starch and xanthan gum. The mass ratio of the acid-hydrolyzed carboxymethyl starch to the xanthan gum was 20:1;

(3) 4.67 g of Tween-80 was added to the compounded solution prepared in the step (2), and after stirring for 30 min, 14.0 g of vitamin E was further added to the mixture, and was stirred for 30 min to form an O/W emulsion. The O/W emulsion was subjected to high-speed shearing using a high-speed shear to obtain a crude emulsion, and the crude emulsion was subjected to high-pressure homogenization to obtain an emulsion. The rate of the high-speed shearing was 20000 r/min, and the shearing time was 2 min. The pressure of the high-pressure homogenization was 40 MPa, and the times of homogenization were 3 times. The emulsion had a solid content of 15%, and a core-to-wall ratio of 1:6;

(4) The emulsion prepared in the step (3) was subjected to spray-drying to obtain the microcapsule encapsulating vitamin E. The process conditions of spray-drying were as follows: an inlet air temperature of 190° C., an outlet air temperature of 80° C., and a feed rate of 400 mL/h.

Example 2

A preparation method of a pH-sensitive microcapsule encapsulating vitamin E, which uses acid-hydrolyzed carboxymethyl starch and xanthan gum as wall materials; wherein acid-hydrolyzed carboxymethyl starch with a degree of substitution of 0.4382 was selected to serve as a raw material, and the microcapsule encapsulating vitamin E was prepared by referring to Example 1 for other conditions.

Example 3

A preparation method of a pH-sensitive microcapsule encapsulating vitamin E, which uses acid-hydrolyzed carboxymethyl starch and xanthan gum as wall materials; wherein acid-hydrolyzed carboxymethyl starch with a degree of substitution of 0.2541 was selected, and the microcapsule encapsulating vitamin E was prepared by referring to Example 1 for other conditions.

Example 4

A preparation method of a pH-sensitive microcapsule encapsulating vitamin E, which uses acid-hydrolyzed carboxymethyl starch and xanthan gum as wall materials; wherein no xanthan gum was added, and the microcapsule encapsulating vitamin E was prepared by referring to Example 1 for other conditions.

Example 5

A preparation method of a pH-sensitive microcapsule encapsulating vitamin E, which uses acid-hydrolyzed carboxymethyl starch and xanthan gum as wall materials; wherein the mass ratio of the acid-hydrolyzed carboxymethyl starch to the xanthan gum was 40:1, and the microcapsule encapsulating vitamin E was prepared by referring to Example 1 for other conditions.

Example 6

A preparation method of a pH-sensitive microcapsule encapsulating vitamin E, which uses acid-hydrolyzed carboxymethyl starch and xanthan gum as wall materials; wherein the mass ratio of the acid-hydrolyzed carboxymethyl starch to the xanthan gum was 10:1; and the microcapsule encapsulating vitamin E was prepared by referring to Example 1 for other conditions.

Figure 2:
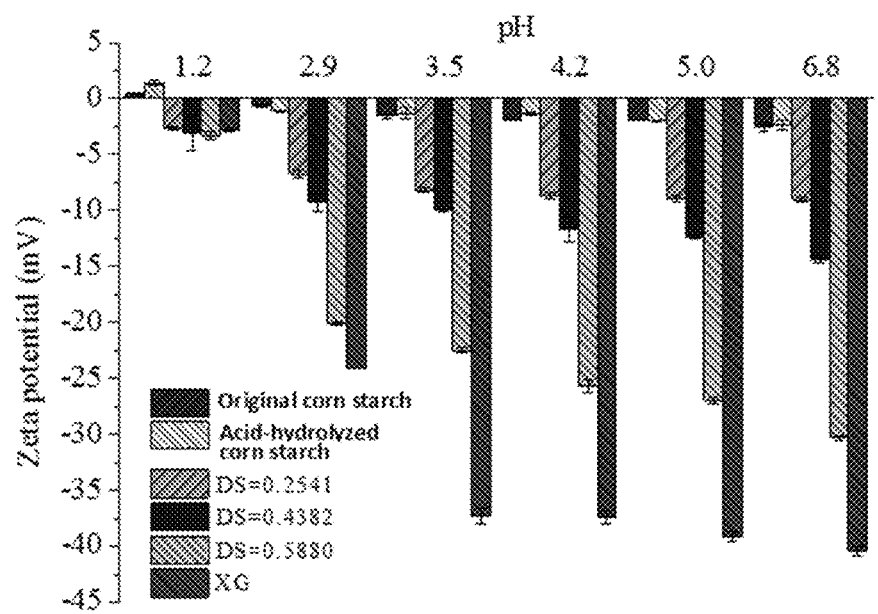
FIG. 2 is a Zeta-potential diagram of an acid-hydrolyzed carboxymethyl starch assembled carrier material under different pH conditions.
Figure 6:
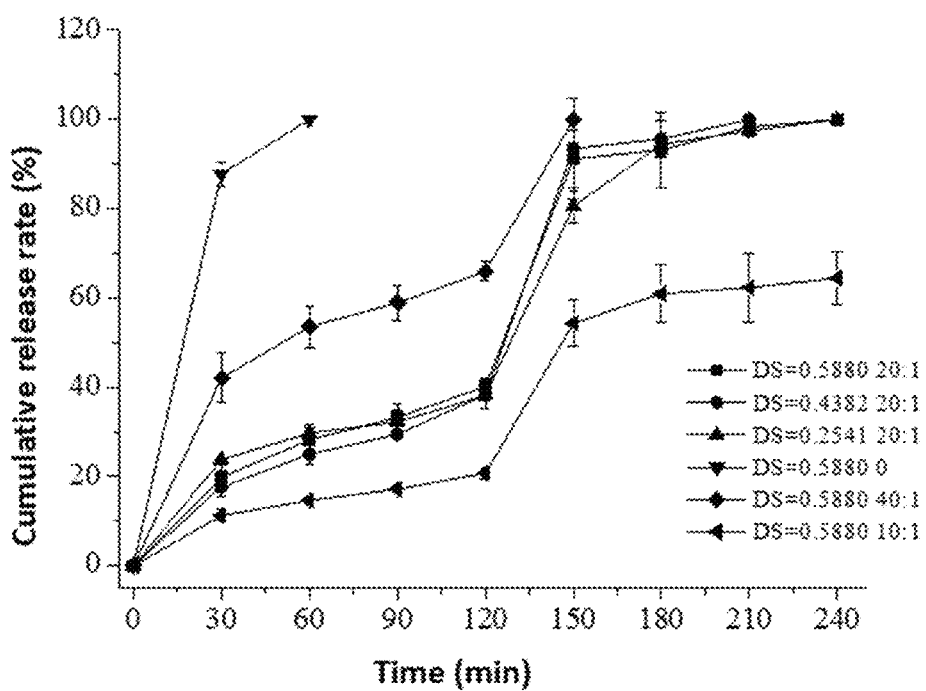
FIG. 6 is a curve graph showing the release of VE encapsulated in a microcapsule wall obtained by compounding acid-hydrolyzed carboxymethyl starch with different degrees of substitution and xanthan gum in different ratios in simulated gastrointestinal juice.

The respective microcapsules are subjected to simulated drug release tests (as shown in FIG. 6), the results of the simulated drug release of the obtained microcapsules are shown in Table 1. When the compounding ratio of starch to hydrophilic colloid is the same, the degree of substitution of the acid-hydrolzed carboxymethyl starch does not significantly affect the release behavior. Comparing the results shows that when the degree of substitution is 0.2541, the best release behavior is obtained. When the degree of substitution of starch is the same, the compounding ratio of starch to hydrophilic colloid significantly affects the release behavior. By investigating the release behavior, it is found that a 20:1 compounding ratio of starch to colloidal is most suitable.

was measured using the Zeta-potentiometer. The test results are shown in FIG. 2, which indicate that the potential of the acid-hydrolzyed carboxymethyl starch changes with the degree of substitution and pH.

Simulated drug release of the microcapsules obtained in Examples 1-6: about 3 g of the microcapsules obtained in Examples 1-6 were dispersed in 900 mL of 37° C. simulated gastric juice and simulated intestinal juice (a phosphate buffer solution containing 450 mg of trypsin) with pH of 1.2 and 6.8, respectively for a continuous simulation test: the rotatory basket was at a rotation speed of 50 rpm, and first in the simulated gastric juice for 2 h, followed by continuous simulation of the small intestine environment for 2 h. 1 mL of the sample was taken out at 0, 30, 60, 90, 120, 150, 180, 210, 240 min, respectively. After vitamin E was extracted with anhydrous ethanol, the content of vitamin E at 285 nm was measured by an ultraviolet spectrophotometer to obtain a cumulative release rate curve of vitamin E in the simulated gastric juice and simulated intestinal juice as shown in FIG. 6. From FIG. 6, it can be found that the microcapsule with better simulated release effect has the mass ratio of starch to xanthan gum of 20:1, and the degree of substitution of starch is 0.2541. The cumulative release rates of the microcapsule in simulated gastric juice and simulated intestinal juice are 38.21% and 61.79%, respectively.

TABLE 1

Drug release capacity of microcapsules prepared from starch raw materials with different degrees of substitution

|  |  | Example 1 | Example 2 | Example 3 | Example 4 | Example 5 | Example 6 |
|---|---|---|---|---|---|---|---|
| Degree of substitution (Compounding ratio of starch to colloidal) |  | 0.5880 (20:1) | 0.4382 (20:1) | 0.2541 (20:1) | 0.5880 (0) | 0.5880 (40:1) | 0.5880 (10:1) |
| Release rate (%) | Gastric juice | 40.15 | 38.32 | 38.21 | 100 | 65.96 | 20.75 |
|  | Intestinal juice | 59.85 | 61.68 | 61.79 | 0 | 34.04 | 43.67 |

The release rate is the mass of vitamin E released in gastric juice or intestinal juice/the mass of vitamin E encapsulated in the microcapsule sample

Example 7

Fourier transform infrared spectroscopy was used to analyze the starch wall material: the resolution was set to 4 cm$^{-1}$, and the air gap was first scanned by a DTGS detector, wherein the scanning wave number was in the range of 4000-400 cm$^{-1}$. After 64 times of scanning, the average value shown by the instrument was the infrared characteristic spectrum of a test sample. The acid-hydrolzyed carboxymethyl starch with three different degrees of substitution, acid-hydrolyzed starch and original starch in Example 1-4 were tested. The test results are shown in FIG. 1, which indicate that carboxymethyl groups have been successfully introduced into the starch molecule by etherification modification.

Zeta-potentiometer was used to analyze the components of the wall material: the potential of the acid-hydrolzyed carboxymethyl starch with three different degrees of substitution, the xanthan gum, the acid-hydrolyzed starch and the original starch in the four Examples at different pH values

Example 8

By referring to Example 1, the effect of solid content on the preparation of the pH-sensitive microcapsule was investigated:

A preparation method of a pH-sensitive microcapsule encapsulating vitamin E, which uses acid-hydrolyzed carboxymethyl starch and xanthan gum as wall materials, and includes the following specific steps:

(1) The xanthan gum was uniformly dispersed in 575.05 g of water and stirred for 90 min to enable the colloid to be uniformly dispersed, so as to obtain a colloidal solution;

(2) The acid-hydrolyzed carboxymethyl starch with a degree of substitution of 0.5880 was weighed, added to the colloidal solution prepared in the step (1) and stirred for 90 min to enable the sample to be uniformly mixed, so as to obtain a compounded solution of acid-hydrolyzed carboxymethyl starch and xanthan gum. The mass ratio of the acid-hydrolyzed carboxymethyl starch to the xanthan gum was 20:1;

(3) 4.67 g of Tween-80 was added to the compounded solution prepared in the step (2); after stirring for 30 min, 14.0 g of vitamin E was further added to the mixture, and was stirred for 30 min to form an O/W emulsion. The O/W emulsion was subjected to high-speed shearing using a high-speed shear to obtain a crude emulsion, and the crude emulsion was subjected to high-pressure homogenization to obtain an emulsion. The rate of the high-speed shearing was 20000 r/min, and the shearing time was 2 min. The pressure of the high-pressure homogenization was 40 MPa, and the times of homogenization were 3 times. The core-to-wall ratio was 1:6, and the solid content of the emulsion was selected from the respective contents in Table 1;

(4) The emulsion prepared in the step (3) was subjected to spray-drying to obtain the microcapsule encapsulating vitamin E. The process conditions of spray-drying were as follows: an inlet air temperature of 190° C., an outlet air temperature of 80° C., and a feed rate of 400 mL/h.

Figure 3:
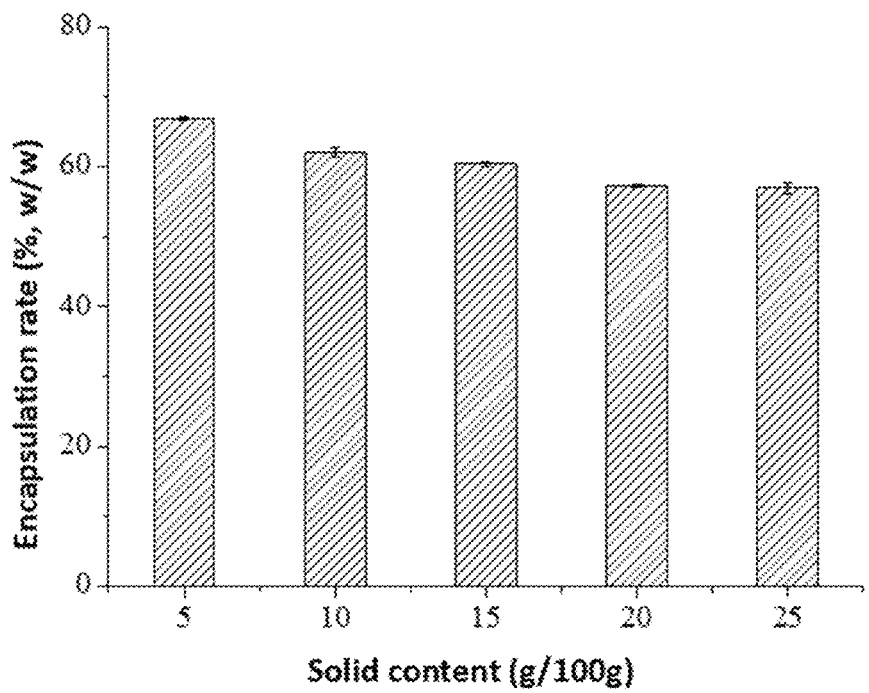
FIG. 3 is a bar graph showing the effect of different solid contents on the encapsulation rate of vitamin E microcapsules.

The encapsulation rate of microcapsules obtained under different solid contents is measured (FIG. 3), and the specific results are shown in Table 2:

TABLE 2

The encapsulation rate of microcapsules obtained under different solids contents

| | Solid content (%) | | | | |
|---|---|---|---|---|---|
| | 5 | 10 | 15 | 20 | 25 |
| Encapsulation rate of microcapsule (%) | 66.76 ± 300.19 | 62.02 ± 300.66 | 60.38 ± 300.30 | 57.32 ± 300.25 | 56.96 ± 300.77 |

The solid content is a percentage of a sum masses of acid-hydrolyzed carboxymethyl starch, xanthan gum (hydrocolloid), vitamin E (fat-soluble substance) and Tween-80 (emulsifier) accounting for the total mass of the emulsion system; and the encapsulation rate of microcapsule is the content of vitamin E encapsulated by the microcapsule/the content of total vitamin E in the microcapsule (the same below).

Example 9

By referring to Example 1, the effect of the content ratio of the core to wall components on the preparation of pH-sensitive microcapsule was investigated:

A preparation method of a pH-sensitive microcapsule encapsulating vitamin E, which uses acid-hydrolyzed carboxymethyl starch and xanthan gum as wall materials, and includes the following specific steps:

(1) 4.0 g of xanthan gum was uniformly dispersed in 575.05 g of water and stirred for 90 min to enable the colloid to be uniformly dispersed, so as to obtain a colloidal solution;

(2) 86.75 g of acid-hydrolyzed carboxymethyl starch with a degree of substitution of 0.5880 was weighed, added to the colloidal solution prepared in the step (1) and stirred for 90 min to enable the sample to be uniformly mixed, so as to obtain a compounded solution of acid-hydrolyzed carboxymethyl starch and xanthan gum. The mass ratio of the acid-hydrolyzed carboxymethyl starch to the xanthan gum was 20:1;

(3) Tween-80 was added to the compounded solution prepared in the step (2); after stirring for 30 min, vitamin E was further added to the mixture, and was stirred for 30 min to form an O/W emulsion. The O/W emulsion was subjected to high-speed shearing using a high-speed shear to obtain a crude emulsion, and the crude emulsion was subjected to high-pressure homogenization to obtain an emulsion. The rate of the high-speed shearing was 20000 r/min, and the shearing time was 2 min. The pressure of the high-pressure homogenization was 40 MPa, and the times of homogenization were 3 times. The solid content of the emulsion was 15%, and the core and wall components were in a ratio selected from the respective ratios in Table 2;

(4) The emulsion prepared in the step (3) was subjected to spray-drying to obtain the microcapsule encapsulating vitamin E. The process conditions of spray-drying were as follows: an inlet air temperature of 190° C., an outlet air temperature of 80° C., and a feed rate of 400 mL/h.

Figure 4:
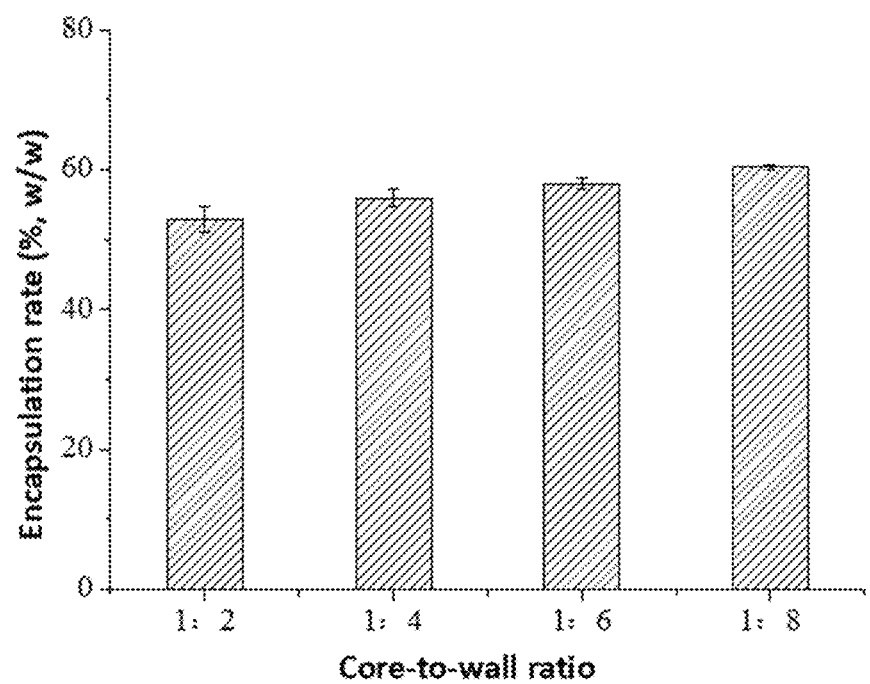
FIG. 4 is a bar graph showing the effect of different core-to-wall ratios on the encapsulation rate of vitamin E microcapsules.

The encapsulation rate of microcapsules obtained under different core-to-wall ratios is measured (FIG. 4), and the specific results are shown in Table 3:

TABLE 3

Encapsulation rate of microcapsules obtained under different core-to-wall ratios

| | Core-to-wall ratio | | | |
|---|---|---|---|---|
| | 1:2 | 1:4 | 1:6 | 1:8 |
| Encapsulation rate of microcapsule | 52.92 ± 1.77 | 55.9 ± 1.22 | 58.01 ± 0.74 | 60.38 ± 0.30 |

Example 10

By referring to Example 1, the effect of the content ratio of xanthan gum to starch on the preparation of pH-sensitive microcapsule was investigated:

A preparation method of a pH-sensitive microcapsule encapsulating vitamin E, which uses acid-hydrolyzed carboxymethyl starch and xanthan gum as wall materials, and includes the following specific steps:

(1) The xanthan gum was uniformly dispersed in 575.05 g of water and stirred for 90 min to enable the colloid to be uniformly dispersed, so as to obtain a colloidal solution;

(2) The acid-hydrolyzed carboxymethyl starch with a degree of substitution of 0.5880 was weighed, added to the colloidal solution prepared in the step (1) and stirred for 90 min to enable the sample to be uniformly mixed, so as to obtain a compounded solution of acid-hydrolyzed carboxymethyl starch and xanthan gum. The mass ratio of the acid-hydrolyzed carboxymethyl starch to the xanthan gum was selected from the respective ratios in Table 3;

(3) 4.67 g of Tween-80 was added to the compounded solution prepared in the step (2); after stirring for 30 min, 14.0 g of vitamin E was further added to the mixture, and was stirred for 30 min to form an O/W emulsion. The O/W emulsion was subjected to high-speed shearing using a high-speed shear to obtain a crude emulsion, and the crude emulsion was subjected to high-pressure homogenization to obtain an emulsion. The rate of the high-speed shearing was 20000 r/min, and the shearing time was 2 min. The pressure of the high-pressure homogenization was 40 MPa, and the times of homogenization were 3 times. The solid content of the emulsion was 15%, and the core-to-wall ratio was 1:6;

(4) The emulsion prepared in the step (3) was subjected to spray-drying to obtain the microcapsule encapsulating vitamin E. The process conditions of spray-drying were as follows: an inlet air temperature of 190° C., an outlet air temperature of 80° C., and a feed rate of 400 mL/h.

Figure 5:
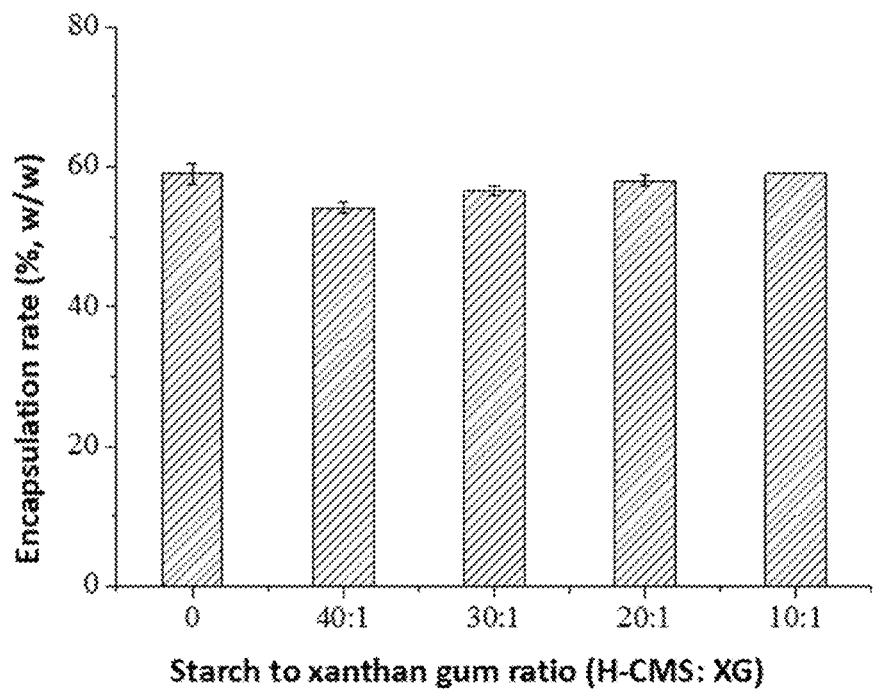
FIG. 5 is a bar graph showing the effect of different xanthan gum to starch ratios on the encapsulation rate of vitamin E microcapsules.

The encapsulation rate of microcapsules obtained under different starch to xanthan gum ratios is measured (FIG. 5), and the specific results are shown in Table 4:

TABLE 4

Encapsulation rate of microcapsules obtained under different starch to xanthan gum ratios

| | 0 (No xanthan gum) | Starch to xanthan gum ratio | | | |
| --- | --- | --- | --- | --- | --- |
| | | 40:1 | 30:1 | 20:1 | 10:1 |
| Encapsulation rate of microcapsule | 59.06 ± 01.46 | 54.12 ± 0.81 | 56.46 ± 0.68 | 58.01 ± 0.74 | 59.04 ± 0.01 |

Example 11

Preparation of a Microcapsule Encapsulating Vitamin E from Debranched Starch and Xanthan Gum:

By referring to Example 1, in the case that the other conditions were the same, debranched starch was compounded with xanthan gum, an emulsifier and vitamin E were added; after drying, a product was obtained. The result shows that the vitamin E encapsulation effect of the product is not as good as the vitamin E encapsulation effect in Example 1. In addition, the release behavior of the product has no pH sensibility.

What is claimed is:

1. A method for preparing a pH-sensitive starch-based microcapsule encapsulating a fat-soluble substance, comprising: performing acid hydrolysis and etherification on starch to obtain acid-hydrolyzed carboxymethyl starch; mixing the acid-hydrolyzed carboxymethyl starch with a hydrophilic colloid to obtain a compounded solution of starch and colloid; and adding an emulsifier and the fat-soluble substance, emulsifying to obtain an emulsion, and drying to obtain the pH-sensitive starch-based microcapsule; wherein a mass fraction ratio of the acid-hydrolyzed carboxymethyl starch to the hydrophilic colloid is (5-40):1.

2. The method according to claim 1, wherein the hydrophilic colloid comprises one or more selected from a group consisting of guar gum, xanthan gum, arabic gum, carrageenan, and gellan gum.

3. The method according to claim 1, wherein a ratio of a mass of the fat-soluble substance to a sum of masses of the acid-hydrolyzed carboxymethyl starch and the hydrophilic colloid in the compounded solution is 1:4 to 1:10.

4. The method according to claim 1, wherein the emulsion has a solid content of 5% to 25%.

5. The method according to claim 1, wherein the fat-soluble substance comprises one or more selected from a group consisting of vitamin E, lycopene, β-carotene, conjugated linoleic acid, docosahexaenoic acid (DHA), and eicosapentaenoic acid (EPA).

6. A pH-sensitive starch-based microcapsule encapsulating a fat-soluble substance, wherein the pH-sensitive starch-based microcapsule is prepared by the method according to claim 1.

7. A nutrient supplement comprising the pH-sensitive starch-based microcapsule according to claim 6.

8. A food additive comprising the pH-sensitive starch-based microcapsule according to claim 6.

9. A method for preparing a pH-sensitive starch-based microcapsule encapsulating a fat-soluble substance, comprising: performing acid hydrolysis and etherification on starch to obtain acid-hydrolyzed carboxymethyl starch; mixing the acid-hydrolyzed carboxymethyl starch with a hydrophilic colloid to obtain a compounded solution of starch and colloid; and adding an emulsifier and the fat-soluble substance, emulsifying to obtain an emulsion, and drying to obtain the pH-sensitive starch-based microcapsule; wherein a ratio of a mass of the fat-soluble substance to a sum of masses of the acid-hydrolyzed carboxymethyl starch and the hydrophilic colloid in the compounded solution is 1:4 to 1:10.

10. The method according to claim 9, wherein the hydrophilic colloid comprises one or more selected from a group consisting of guar gum, xanthan gum, arabic gum, carrageenan, and gellan gum.

11. The method according to claim 9, wherein a mass fraction ratio of the acid-hydrolyzed carboxymethyl starch to the hydrophilic colloid is (5-40):1.

12. The method according to claim 9 wherein the emulsion has a solid content of 5% to 25%.

13. The method according to claim 9, wherein the fat-soluble substance comprises one or more selected from a group consisting of vitamin E, lycopene, β-carotene, conjugated linoleic acid, docosahexaenoic acid (DHA), and eicosapentaenoic acid (EPA).

14. A pH-sensitive starch-based microcapsule encapsulating a fat-soluble substance, wherein the pH-sensitive starch-based microcapsule is prepared by the method according to claim 9.

15. A nutrient supplement comprising the pH-sensitive starch-based microcapsule according to claim 14.

16. A food additive comprising the pH-sensitive starch-based microcapsule according to claim 14.

* * * * *